United States Patent [19]

Nickolson et al.

[11] 4,348,327
[45] Sep. 7, 1982

[54] PROCESS FOR THE PREPARATION OF 17α-HYDROXY- AND 17Aα-HYDROXY-D-HOMOETIOCARBOXYLIC ACIDS

[75] Inventors: Robert Nickolson; Ulrich Kerb; Rudolf Wiechert, all of Berlin, Fed. Rep. of Germany; Leo Alig, Kaiseraugst, Switzerland; Andor Fürst, Basel, Switzerland; Marcel Müller, Frenkendorf, Switzerland

[73] Assignee: Schering Aktiengesellschaft, Berlin & Bergkamen, Fed. Rep. of Germany

[21] Appl. No.: 276,563

[22] Filed: Jun. 23, 1981

[30] Foreign Application Priority Data

Jun. 24, 1980 [DE] Fed. Rep. of Germany ....... 3024008

[51] Int. Cl.³ .............................................. C07J 9/00
[52] U.S. Cl. .................................................. 260/397.1
[58] Field of Search ...................................... 260/397.1

[56] References Cited

U.S. PATENT DOCUMENTS

| 4,119,625 | 10/1978 | Schmidlin | 260/397.1 |
| 4,163,744 | 8/1979 | Kaiser | 260/397.1 |
| 4,278,669 | 7/1981 | Alvarez | 260/397.1 |
| 4,285,937 | 8/1981 | Kalvoda | 260/397.1 |

*Primary Examiner*—Elbert L. Roberts
*Attorney, Agent, or Firm*—Millen & White

[57] ABSTRACT

17α-hyroxy- and 17aα-hydroxy-D-homoetiocarboxylic acids of the formula

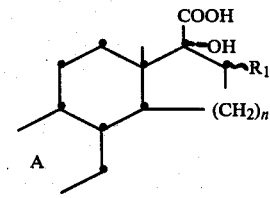

wherein
n is 1 or 2,
A is

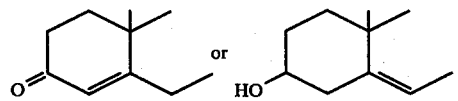

and
$R_1$ is H or $CH_3$ are prepared by hydrating the corresponding 17-nitriles with a mixture of a lower carboxylic acid and its anhydride in the presence of perchloric acid. The resultant 17β-N-acylcarboxamide is then treated with an alkali metal hydroxide in a polyhydric alcohol at an elevated temperature. The product acids are intermediates, e.g., for the production of steroids having antiinflammatory activity.

10 Claims, No Drawings

PROCESS FOR THE PREPARATION OF 17α-HYDROXY- AND 17Aα-HYDROXY-D-HOMOETIOCARBOXYLIC ACIDS

BACKGROUND OF THE INVENTION

The present invention relates to a method of preparing 17α-hydroxy and 17aα-hydroxy-D-homoetiocarboxylic acids.

According to the works of Miescher et al., Helv. 21: 1317 (1938), hydroxy-17-carboxylic acids of the androstane series, having an unnatural configuration at the C-17 carbon atom, can be produced in a three-stage process by the hydration of 17-cyanohydrin derivatives. In this method, the carbonitrile is treated in the first stage with hydrogen chloride/ethanol, thus forming the 3β-acetoxy-17-hydroxy-5α-chloroandrostane-17-carboxylic acid amide.

In the second stage, the thus-formed hydroxyamide is refluxed with methanolic potassium hydroxide solution, thus obtaining the 3β,17-dihydroxy-5-androstene-17-carboxylic acid amide. In the third stage, the dihydroxyamide is hydrolyzed to the free carboxylic acid with sodium propylate.

However, this process is disadvantageous in that the desired acid is obtained only in very low yields. However, recent experiments repeating this process were not very successful.

SUMMARY OF THE INVENTION

Accordingly, it is an object of the present invention to provide a process for preparing such acids in higher yields and requiring fewer reaction steps.

Upon further study of the specification and appended claims, further objects and advantages of this invention will become apparent to those skilled in the art.

These objects have been attained by this invention by conducting the hydration of the cyanohydrin at room temperature with a mixture of a lower carboxylic acid and its anhydride in the presence of perchloric acid, thus forming the corresponding 3α,17β-diacyloxy-5-androstene-17β-N-acylcarboxamide and/or its D-homo-homolog and thereafter treating the thus-produced α-acylamide in a polyhydric alcohol with an alkali hydroxide at an elevated temperature.

Thus, this invention relates to a process for preparing 17α-hydroxy- and 17aα-hydroxy-D-homoetiocarboxylic acids of the formula

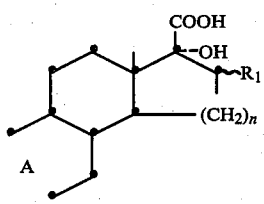

wherein
n is 1 or 2,
A is

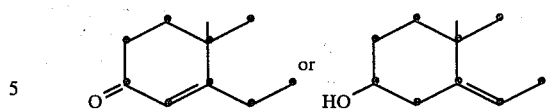

and
$R_1$ is H or $CH_3$,
comprising hydrating the corresponding nitriles of the formula

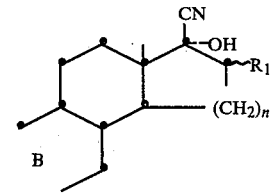

wherein
$R_1$ and n are as defined above and
B is

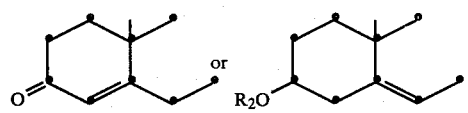

wherein $R_2$ is hydrogen or a lower acyl residue of up to 6 carbon atoms, with a mixture of a lower carboxylic acid and its anhydride in the presence of perchloric acid at room temperature, and thereafter treating the thus-formed 17β-N-acylcarboxamide in a polyhydric alcohol with an alkali hydroxide at an elevated temperature.

DETAILED DISCUSSION

The course of the reaction of this invention is surprising since it would have been expected, in view of the above-cited works by Miescher et al, that the cyanohydrin diacylates would have been formed, rather than the acylamides which of course, are also acylated at the OH groups.

For $R_4$, lower acyl residues include those derived from physiologically compatible aliphatic carboxylic acids, e.g., acetic, propionic, butyric, isobutyric and caproic acid, i.e. alkanoyl groups.

The process is conducted in the first step in a mixture of lower alkyl carboxylic acids and lower alkyl acid anhydrides in a molar ratio of acid to anhydride of 0.1:100, preferably 1:1, and in a total quantity of 1.1–10 molar equivalents in total, per equivalent of steroid. The number of C-atoms in the alkyl moieties is 1–10. The perchloric acid added as the acidic catalyst is admixed in an amount of 0.001–0.1, preferably 0.01 molar equivalent, per molar equivalent of the steroid. Room temperature is preferred; suitable temperatures include 5°–50° C. Preferably, the acid anhydride corresponds to the acid used. Reaction times are generally 0.5–5 hours.

The thus-formed acylamide can be readily separated by conventional crystallization and then used in the subsequent reaction stage. In the latter, the acylamide is heated for a prolonged period (e.g., 10–200 hours) in a polyhydric alcohol, such as ethylene glycol or glycerin, with an alkali metal hydroxide, such as potassium or sodium hydroxide. Typical amounts of these are 0.5–5 molar equivalents of the polyhydric alcohol and 5–50 molar equivalents of the hydroxide, both per molar equivalent of the acylamide. Temperatures above 100° C. are suitable, e.g., 100°–200° C. In this connection, the use of autoclaves and a protective gas, such as nitrogen, have proved to be advantageous.

It is not necessary to carry out this subsequent treatment to form the 17-carboxylic acid in one step. This can be accomplished, instead, e.g., via the intermediate stage of the acid amide wherein the acylated OH groups are unblocked. The selective deacylation can be effected by treating the OH-acylated N-acylcarboxamide with a methanolic alkali metal hydroxide solution, such as potassium hydroxide solution at room temperature. The acid is thus prepared by treatment with the mentioned hydroxide polyhydric alcohol reagent. However, the direct reaction of the N-acylcarboxamide product of the first step to the carboxylic acid is preferred without isolation of the intermediate acid amide.

The compounds prepared by this invention are intermediates for the preparation of corticoids and antiinflammatorily active steroids (see, for example, DOS's [German Unexamined Laid-Open Applications] Nos. 2,538,627; 2,539,595; and 2,614,079). The starting materials are all conventional per se and can be prepared by conventional methods also using conventional starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

A solution of 3.57 g of 3β-acetoxy-17α-hydroxy-5-androstene-17-carbonitrile in 25 ml of glacial acetic acid and 25 ml of acetic anhydride is combined with 0.71 ml of 70% strength perchloric acid, and the mixture is stirred for 1 hour at 20° C. The product is precipitated into ice water and extracted with methylene chloride and ethyl acetate. The organic phases are washed with semisaturated sodium bicarbonate solution and then with water. After drying over sodium sulfate, the solution is extensively concentrated under vacuum, and the residue is recrystallized from methanol, thus obtaining 3.41 g of 3β,17α-diacetoxy-5-androstene-17-N-acetylcarboxamide, mp 208.5°–209.5° C.

A

A solution of 1.65 g of 3β,17α-diacetoxy-5-androstene-17-N-acetylcarboxamide in 100 ml of methanol is combined with 11 ml of 1 N potassium hydroxide solution, and the mixture is stirred under argon at room temperature for 22 hours. The thus-crystallized product is vacuum-filtered and washed with 60% methanol-water, thus producing 1.26 g of 3β,17α-dihydroxy-5-androstene-17β-carboxylic acid amide, mp 308° C. (decomposition).

A solution of 1.10 g of 3β,17α-dihydroxy-4-androstene-17β-carboxylic acid amide in 150 ml of ethylene glycol is combined with a solution of 3.2 g of potassium hydroxide in 7.0 ml of water and allowed to react in a tumbling autoclave. The reaction mixture is cooled to 20° C. and diluted with 70 ml of methanol. For purification purposes this solution is passed through an anion exchange column, and the neutral proportion is separated by washing with 600 ml of methanol. The column is then eluted with 80% methanol—2 N hydrochloric acid solution. The fractions are combined and the excess solvent gently concentrated at 30° C. under vacuum. The crystallized product is vacuum-filtered, washed with 10% methanol—water mixture, and dried, thus obtaining 920 mg of 3β,17α-dihydroxy-5-androstene-17-carboxylic acid, mp 236.5°–237.5° C.

B

A solution of 500 mg of 3β,17α-diacetoxy-5-androstene-17-N-acetylcarboxamide in 70 ml of ethylene glycol is combined with a solution of 1.2 g of potassium hydroxide in 3.5 ml of water, and the mixture is treated as described above in a tumbling autoclave under nitrogen for 72 hours at 170° C., and then worked up. Yield: 330 mg of 3β,17α-dihydroxy-5-androstene-17-carboxylic acid, mp 236.5°–237° C.

EXAMPLE 2

A solution of 6.26 g of 17α-hydroxy-17-cyano-4-androsten-3-one in 50 ml of glacial acetic acid and 50 ml of acetic anhydride is combined with 0.5 ml of 70% perchloric acid, and the mixture is allowed to stand for 1 hour at 20° C. The product is precipitated into ice water, filtered off, and then dissolved in 570 ml of methanol. This solution is combined with 61 ml of a 1 N potassium hydroxide solution, and the mixture is stirred overnight at 20° C. The methanolic solution is diluted with 500 g of ice water, the precipitated product is vacuum-filtered and dried. Repeated crystallization from ethyl acetate—methylene chloride yields 5.62 g of 17α-hydroxy-3-oxo-4-androstene-17-carboxylic acid amide, mp 271°–273.5° C.

A solution of 500 mg of 17α-hydroxy-3-oxo-4-androstene-17-carboxylic acid amide is treated and worked up analogously to Example 1, thus obtaining, after recrystallization of the crude product from ethyl acetate, 410 mg of 17α-hydroxy-3-oxo-4-androstene-17-carboxylic acid, mp 233°–234° C.

EXAMPLE 3

A solution of 2.3 g of 3β,17α-dihydroxy-16α-methyl-5-androstene-17β-carbonitrile in 17.5 ml of acetic anhydride and 17.5 ml of acetic acid is combined with 0.18 ml of 70% perchloric acid and stirred for 1 hour at 25° C. The product is precipitated into water, vacuum-filtered, washed with water, and dried. Yield: 3.10 g of 3β,17α-diacetoxy-16α-methyl-5-androstene-17-N-acetylcarboxamide, mp 105.5°–108° C.

A solution of 720 mg of 3β,17α-diacetoxy-16α-methyl-5-androstene-17-N-acetylcarboxamide in 70 ml of ethylene glycol is combined with 1.8 g of potassium hydroxide in 5 ml of water, and the mixture is heated for 80 hours in a tumbling autoclave to 150° C. After the reaction mixture has been worked up as described in Example 1, 315 mg of 3β,17α-dihydroxy-16α-methyl-5-androstene-17β-carboxylic acid is obtained, mp 258° C. (decomposition).

EXAMPLE 4

A solution of 1.20 g of 3β-acetoxy-17α-hydroxy-16β-methyl-5-androstene-17-carbonitrile is treated and worked up analogously to Example 3. Recrystallization from acetone-ethyl acetate yields 720 mg of 3β,17α- dihydroxy-16β-methyl-5-androstene-17-carboxylic acid, mp 214°–216° C.

EXAMPLE 5

A suspension of 357 mg of 3β-acetoxy-17α-hydroxy-5-androstene-17β-carbonitrile in 5.0 ml of propionic acid and 5.0 ml of propionic anhydride is combined with 0.1 ml of 70% perchloric acid, and the mixture is allowed to react for 65 minutes at room temperature. The solution is then precipitated into water and extracted with methylene chloride. The organic phases are washed neutral with water, dried over sodium sulfate, and concentrated. The thus-obtained crude product is chromatographed over silica gel with a methylene chloride/acetone gradient and the product is recrystallized from methanol, thus obtaining 282 mg of 3β-acetoxy-17α-propionyloxy-5-androstene-17β-N-propionylcarboxamide, mp 96°–102° C.

This product is converted analogously to Example 1(A) or 1(B) into 3β,17α-dihydroxy-5-androstene-17-carboxylic acid, mp 236°–238° C.

EXAMPLE 6

Analogously to Example 5, 357 mg of 3β-acetoxy-17α-hydroxy-5-androstene-17β-carbonitrile in 5.0 ml of isobutyric acid and 5.0 ml of isobutyric anhydride is combined with 0.1 ml of 70% perchloric acid, and the mixture is stirred for 1 hour at room temperature. After the product has been worked up and purified as described in Example 5, the yield is 223 mg of 3β-acetoxy-17α-isobutyryloxy-5-androstene-17β-N-isobutyrylcarboxamide, mp 135°–142° C.

This product is converted analogously to Example 1(A) or 1(B) into 3β,17α-dihydroxy-5-androstene-17-carboxylic acid, mp 237°–238.5° C.

EXAMPLE 7

A solution of 1.0 g of 3β-acetoxy-17aα-hydroxy-D-homo-5-androstene-17aβ-carbonitrile (produced in analogy to the procedure described in J. Fried and J. A. Edwards, Organic Reactions in Steroid Chemistry, Van Nostrand Reinhold Co., New York, 1972, vol. II; mp 200°–205° C. with decomposition) in 7 ml of acetic acid and 7 ml of acetic anhydride is combined with 0.2 ml of 70% perchloric acid and allowed to react for 65 minutes. The product is precipitated into ice water and vacuum-filtered. Chromatography and crystallization from hexane yield 878 mg of 3β,17aα-diacetoxy-D-homo-5-androstene-17a-N-acetylcarboxamide, mp 162°–163° C.

A suspension of 2.08 g of 3β,17aα-diacetoxy-D-homo-5-androstene-17a-N-acetylcarboxamide in 126 ml of methanol is combined with 13.9 ml of 1 N potassium hydroxide solution and stirred for 18 hours at 20° C. The precipitated product is then vacuum-filtered and washed with 60% methanol. Yield: 1.52 g of 3β,17aα-dihydroxy-D-homo-5-androstene-17aβ-carboxamide, mp 310°–312° C. (decomposition).

A solution of 2.97 g of 3β,17aα-dihydroxy-D-homo-5-androstene-17aβ-carboxamide in 420 ml of ethylene glycol is combined with a solution of 4.8 g of potassium hydroxide in 21 ml of water, and the mixture is maintained for 96 hours under nitrogen at 165° C. in a tumbling autoclave. The reaction solution is cooled to 20° C. After adding 420 ml of 90% methanol, the mixture is passed through an anion exchange column, and the neutral proportion is separated with about 4 l of 90% methanol-water mixture. The column is then eluted with 80% methanol-2 N hydrochloric acid solution. The fractions are combined and gently concentrated at 30° C. under vacuum. The thus-crystallized product is vacuum-filtered, washed with 10% methanol-water, and dried, thus obtaining 2.56 g of 3β,17aα-dihydroxy-D-homo-5-androstene-17aβ-carboxylic acid, mp 248°–249° C. (decomposition).

EXAMPLE 8

A solution of 500 mg of 3β-acetoxy-17aα-hydroxy-D-homo-5-androstene-17aβ-carbonitrile in 3.5 ml of acetic acid and and 3.5 ml of acetic anhydride is combined with 0.1 ml of 70% perchloric acid and stirred for 75 hours at 20° C. After the mixture has been worked up as described in Example 1, the crude product (700 mg) is dissolved without purification in 70 ml of ethylene glycol and combined with 1.2 g of potassium hydroxide in 3.5 ml of water. The further treatment and working up operation takes place as described in Example 3. Yield: 425 mg of 3β,17aα-dihydroxy-D-homo-5-androstene-17aβ-carboxylic acid, mp 248°–249.5° C. (decomposition).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 17α-hydroxy- or 17aα-hydroxy-D-homoetiocarboxylic acid of the formula

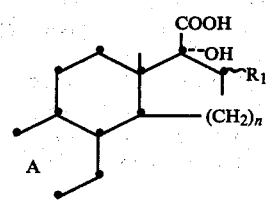

wherein
n is 1 or 2,
A is

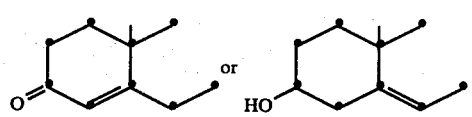

and
$R_1$ is H or $CH_3$,
comprising hydrating the corresponding nitrile of the formula wherein
R₁ and n are as defined above and
B is wherein R₂ is hydrogen or $C_{1-6}$ alkanoyl, with a mixture of a lower alkane carboxylic acid and its anhydride in the presence of perchloric acid,
  and subsequently treating the thus-formed 17β-N-acylcarboxamide in a polyhydric alcohol with an alkali metal hydroxide at a temperature of 100° C. or higher.

2. A process of claim 1 wherein the hydration step is conducted at room temperature.

3. A process of claim 1 or 2 wherein the molar ratio in the hydration step is 0.1:100 and the total quantity of such acid and anhydride is 1.1–10 molar equivalents per equivalent of starting steroidal acid.

4. A process of claim 3 wherein the amount of perchloric acid in the hydration step is 0.001–0.1 molar equivalents per molar equivalent of starting steroidal acid.

5. A process of claim 1 or 2 wherein the lower alkane carboxylic acid is acetic acid and the corresponding anhydride is acetic anhydride.

6. A process of claim 1 wherein prior to the treatment with polyhydric alcohol and alkali metal hydroxide, the 17β-N-acylcarboxamide is first treated with methanolic alkali metal hydroxide to deacylate any blocked OH groups.

7. A process of claim 1 wherein the polyhydric alcohol is ethylene glycol or glycerine.

8. A process for preparing a etiocarboxylic acid or a D-homo-counterpart of the formula wherein
n is 1 or 2,
A is R₁ is H or CH₃, and
R₃ and R₄ independently each are $C_{1-6}$-alkanoyl comprising hydrating the corresponding nitrile of the formula wherein
R₁ and n are as defined above and
B is wherein R₂ is hydrogen or $C_{1-6}$ alkanoyl, with a mixture of the corresponding $C_{1-6}$ alkane carboxylic acid and its anhydride in the presence of perchloric acid at room temperature.

9. A process of claim 1 wherein R₁ is CH₃.

10. A process of claim 1 wherein R₁ is H.

* * * * *